United States Patent [19]
Brewster et al.

[11] Patent Number: 5,922,308
[45] Date of Patent: Jul. 13, 1999

[54] UNDERARM COMPOSITIONS

[75] Inventors: David Allen Brewster; Brian John Dobkowski, both of Shelton; Francis Jones, Guilford; Steven Anthony Orofino, Stratford, all of Conn.

[73] Assignee: Chesebrough-Pond's USA Co.,, Greenwich, Conn.

[21] Appl. No.: 08/821,282

[22] Filed: Mar. 20, 1997

Related U.S. Application Data

[60] Provisional application No. 60/020,743, Jun. 28, 1996.

[51] Int. Cl.$^6$ .................. A61K 7/37; A61K 7/00
[52] U.S. Cl. ................. 424/65; 424/66; 424/67; 424/68; 424/400; 424/401
[58] Field of Search ................. 424/65, 66, 67, 424/68, 400, 401

[56] References Cited

U.S. PATENT DOCUMENTS

| | | | |
|---|---|---|---|
| 4,526,780 | 7/1985 | Marschner et al. | 424/66 |
| 4,673,570 | 6/1987 | Soldati | 424/66 |
| 4,720,353 | 1/1988 | Bell | 252/309 |
| 4,742,142 | 5/1988 | Shimizu et al. | 528/15 |
| 4,840,789 | 6/1989 | Orr et al. | 424/66 |
| 4,937,069 | 6/1990 | Shin | 424/66 |
| 4,970,252 | 11/1990 | Sakuta et al. | 524/268 |
| 4,980,167 | 12/1990 | Harashima et al. | 424/401 |
| 4,983,418 | 1/1991 | Murphy et al. | 424/47 |
| 4,987,169 | 1/1991 | Kuwata et al. | 524/267 |
| 5,019,375 | 5/1991 | Tanner et al. | 424/66 |
| 5,069,897 | 12/1991 | Orr | 424/66 |
| 5,102,656 | 4/1992 | Kasat | 424/66 |
| 5,143,722 | 9/1992 | Hollenberg et al. | 424/63 |
| 5,145,933 | 9/1992 | Grisoni et al. | 528/15 |
| 5,156,834 | 10/1992 | Beckmeyer et al. | 424/47 |
| 5,225,188 | 7/1993 | Abrutyn et al. | 424/66 |
| 5,236,986 | 8/1993 | Sakuta | 524/267 |
| 5,266,321 | 11/1993 | Shukuzaki et al. | 424/401 |
| 5,280,019 | 1/1994 | Klimisch | 514/63 |
| 5,302,378 | 4/1994 | Crotty et al. | 424/59 |
| 5,387,417 | 2/1995 | Rentsch | 424/401 |
| 5,623,017 | 4/1997 | Hill | 524/860 |
| 5,654,362 | 8/1997 | Schulz, Jr. et al. | 524/862 |

FOREIGN PATENT DOCUMENTS

| | | |
|---|---|---|
| 0 295 886 | 6/1988 | European Pat. Off. . |
| 0 473 039 | 8/1991 | European Pat. Off. . |
| 3-197413 | 12/1989 | Japan . |
| WO 96/018374 | 6/1996 | WIPO . |
| 97/44010 | 11/1997 | WIPO . |
| 98/04236 | 2/1998 | WIPO . |

OTHER PUBLICATIONS

GE Silicones Material Safety Data Sheet Jul. 24, 1996.

*Primary Examiner*—Shelley A. Dodson
*Attorney, Agent, or Firm*—Milton L. Honig

[57] ABSTRACT

A underarm treatment composition is provided including a deodorant and/or antiperspirant active, a crosslinked non-emulsifying siloxane elastomer and a volatile siloxane. The compositions were found not to undergo syneresis. They also have improved efficacy, faster absorption, anti-whitening and other properties.

14 Claims, No Drawings

UNDERARM COMPOSITIONS

This application claims benefit of U.S. provisional application 60/020,743, filed Jun. 28, 1996.

BACKGROUND OF THE INVENTION

1. Field of the Invention

The invention relates to underarm compositions having deodorancy and/or perspiration inhibiting properties.

2. The Related Art

Deodorant/antiperspirant compositions in the form of creams are known in the art. Primarily they have been oil-in-water or water-in-oil emulsions. Although these provide convenient vehicles for delivery of deodorant/antiperspirant actives, emulsions generally tend to produce undesirable sensations on the skin. They are sticky and feel wet. Oil continuous emulsions require shaking and feel oily upon application. Any water system also requires time to dry on the skin.

Anhydrous antiperspirant/deodorant creams have been reported in U.S. Pat. No. 5,102,656 (Kasat). A creamy, heterogeneous anhydrous product is described whose ingredients include a volatile silicone carrier, a gelling agent such as castorwax and a physiologically acceptable antiperspirant agent.

Cream type products are also described in U.S. Pat. No. 5,069,897 (Orr) and U.S. Pat. No. 4,840,789 (Orr et al.). Both of these patents formulate a cream with a volatile silicone oil, a non-volatile liquid emollient (e.g. $C_{12}$–$C_{25}$ hydrocarbon or non-volatile silicone), a particulate thickening material (e.g. colloidal silica) and a particulate antiperspirant active material. Related technology although not in cream form is found in U.S. Pat. No. 5,156,834 (Beckmeyer et al.).

U.S. Pat. No. 4,937,069 (Shin) discloses a substantially anhydrous semi-solid antiperspirant whose components include an antiperspirant active, fumed silica, a thickening/solid emollient (particularly a wax of melting point 20 to 120° C.), cyclomethicone and dimethicone.

U.S. Pat. No. 4,526,780 (Marschner et al.) achieves a stable anhydrous cream composition of ultra dry characteristics through use of a gelatinized clay in combination with a deodorant active agent, an oil absorbent powder (e.g. talc, starch, etc.) and a volatile silicone.

Ultra dry creams as described in the above patents present a considerable advance in the art. However, further improvements would be useful with respect to enhancing rate of absorption, dry feel, reduced stickiness or greasiness, rapid drying time, better spreadability and improved deodorant/antiperspirant activity. Most important is to solve the problem of syneresis, the breakdown of an initially relatively thick product into a much less viscous one. Syneresis results in breakdown liquids having a tendency to leak from typical packaging for such products.

Accordingly, it is an object of the present invention to provide an underarm product, especially a cream, of enhanced aesthetics including faster absorption, dry feel, non-whitening, reduced stickiness or greasiness, rapid drying time, better spreadability and effectiveness as a deodorant active.

Still another object of the present invention is to provide an underarm product, especially a cream, exhibiting a reduced level of syneresis and thereby avoiding any leakage of product from its packaging.

These and other objects of the present invention will become more readily apparent from review of the subsequent summary, detailed description and examples.

SUMMARY OF THE INVENTION

An underarm treatment composition is provided that includes:

(i) an underarm active present in an effective amount to inhibit odor or to reduce perspiration;

(ii) from 0.1 to 30% by weight of a crosslinked non-emulsifying siloxane elastomer, (iii) from 10 to 80% by weight of a volatile siloxane.

DETAILED DESCRIPTION OF THE INVENTION

Now it has been discovered that an ultradry deodorant/antiperspirant composition of enhanced properties can be achieved through incorporation of a crosslinked non-emulsifying siloxane elastomer in combination with a volatile silicone. One of the main advantages is that when the elastomer swells in the volatile siloxane (e.g. cyclomethicone), the resultant composition does not cause syneresis that would normally cause leakage problems. Furthermore, the elastomer thickens the cyclomethicone thus eliminating the need for other thickeners that could reduce efficacy. Generally the aesthetics of the resultant product are superior to those of commercial products. Application is also smooth and dry.

A first essential element of compositions according to the present invention is that of a deodorant and/or antiperspirant active. Most preferable is an astringent salt which combines the properties of deodorancy and antiperspirancy. Suitable astringents may be inorganic or organic salts of aluminum, zirconium, zinc and mixtures thereof. Salts useful as astringents or as components of astringent complexes include aluminum halides, aluminum hydroxyhalides, zirconyl oxyhalides, zirconyl hydroxyhalides and mixtures of these salt materials.

Aluminum salts of this type include aluminum chloride and the aluminum hydroxyhalides having the general formula $Al_2(OH)_xQ_y$—$XH_2O$ where Q is chlorine, bromine or iodine, where x is 2 to 5 and x+y=6 and x and y do not need to be integers; and where X is about 1 to 6.

Zirconium compounds which are useful may be represented by the following general empirical formula: $ZnO(OH)_{2-nz}B_z$, wherein z may vary from about 0.9 to 2 and need not be an integer, n is the valence of B, 2−nz is greater than or equal to 0, and B may be selected from the group consisting of halides, nitrate, sulfamate, sulfate and mixtures thereof. As with the basic aluminum compounds, it will be understood that the aforementioned formula is greatly simplified and is intended to represent and include compounds having coordinated and/or bound water in various quantities, as well as polymers, mixtures and complexes of the above. Zirconium hydroxy salts actually represent a range of compounds having various amounts of the hydroxy group, varying from about 1.1 to only slightly greater than 0 groups per molecule.

Several types of deodorant complexes utilizing the above astringent salts are known in the art. For example, U.S. Pat. No. 3,792,068 (Luedders et al.), discloses complexes of aluminum, zirconium and amino acids such as glycine. Complexes reported therein and similar structures are commonly known as ZAG. The ZAG complexes ordinarily have an Al:Zr ratio of from about 1.67 to 12.5 and a Metal:Cl ratio of from about 0.73 to 1.93. A preferred aluminum compound for preparation of ZAG type complexes is aluminum chlorhydroxide of the empirical formula $Al_2(OH)_5Cl\cdot 2H_2O$. Preferred zirconium compounds for preparation of ZAG-type complexes are zirconyl hydroxychloride having the empirical formula $ZrO(OH)Cl \cdot 3H_2O$ and the zirconyl hydroxyhalides of the empirical formula $ZrO(OH)_{2-a}Cl_2 \cdot nH_2O$ wherein a is from 1.5 to 1.87 and n is from about 1 to 7. The preferred amino acid for preparing such ZAG-type complexes is glycine of the formula $CH_2(NH_2)COOH$. Spherical ZAG, with particle size 1 to 100 microns, is especially preferred.

Amounts of the deodorant/antiperspirant active may range from 0.1 to 70%. When the active is an astringent salt, the amounts may range from about 1% to 70%, preferably from 15% to 60% by weight calculated on an anhydrous metal salt basis (exclusive of glycine, the salts of glycine or other complexing agents).

Deodorant actives according to the present invention also include materials other than those functioning as antiperspirants. Deodorants should be capable of killing or hindering the growth of microorganisms that generate malodor or that promote the decomposition of body oils into odiferous fatty acids. Most prominent among organic antimicrobial materials are triclosan, triclorban, chlorhexedine and certain fragrant oils known as deo perfumes (e.g. U.S. Pat. No. 4,278,658 to Hooper et al.). Amounts of the organic antimicrobial materials may range from 0.01 to 1%, preferably 0.1 to 0.5% by weight. Inorganic antimicrobial materials may also serve as deodorant actives. These include zinc oxide, zinc hydroxide, zinc carbonate, zinc phenolsulfonate, magnesium oxide, magnesium hydroxide, magnesium carbonate, lanthanum oxide, lanthanum hydroxide, lanthanum carbonate, sodium bicarbonate and combinations thereof. Amounts of the inorganic materials may range from 0.1 to 60% by weight.

Crosslinked non-emulsifying siloxane elastomers are the second essential element of this invention. They will have an average number molecular weight in excess of 2,000, preferably in excess of 1,000,000 and optimally will range from 10,000 to 20 million. The term "non-emulsifying" defines a siloxane from which polyoxyalkylene units are absent. Advantageously the elastomers are formed from a divinyl monomer reacting with Si—H linkages of a siloxane backbone. Elastomer compositions are commercially available from the General Electric Company under product designation General Electric Silicone 1229 with proposed CTFA name of Cyclomethicone and Vinyl Dimethicone/Methicone Cross Polymer, delivered as 20–35% elastomer in a cyclomethicone carrier. A related elastomer composition under the CTFA name of Crosslinked Stearyl Methyl Dimethyl Siloxane Copolymer is available as Gransil SR-CYC (25–35% elastomer in cyclomethicone) from Grant Industries, Inc., Elmwood Park, N.J. The commercial products from General Electric and Grant Industries ordinarily are further processed by subjecting them to a high pressure (approximately 1,500 to 3,500 psi) treatment in a Sonolator with recycling in 10 to 60 passes. Sonolation achieves a resultant fluid with elastomer average particle size ranging from 0.2 to 10 micron, preferably 0.5 to 5 micron. Viscosity is best when ranging between 300 and 20,000 cps at 25° C. as measured by a Brookfield LV Viscometer (size 4 bar, 60 rpm, 15 sec.).

Amounts of the elastomer may range from 0.1 to 30%, optimally from 1 to 15%, most preferably from 3 to 10% by weight.

A third essential element to be incorporated into the compositions of this invention is that of a volatile siloxane. This material may be present in amounts from 10 to 80%, preferably from 20 to 60%, optimally from 30 to 50% by weight.

The term "volatile" refers to those materials having a measurable pressure at ambient conditions. Volatile polyorganosiloxanes useful herein may be cyclic or linear. Preferred cyclic silicones include polydimethylsiloxanes containing from about 3 to about 9 silicon atoms, preferably containing from about 4 to about 5 silicon atoms, generally known as cyclomethicones. Preferred linear silicone oils include the polydimethylsiloxanes containing from about 3 to about 9 silicon atoms. The linear volatile silicones generally have viscosities of less than about 5 centistokes at 25° C., while the cyclic materials have viscosities of less than about 10 centistokes, the preferable range being from 0.1 to 8 centistokes. Examples of silicone oils useful in the present invention include: Dow Corning 244, Dow Corning 245, Dow Corning 344, Dow Corning 345 and Dow Corning 200 (manufactured by the Dow Corning Corporation); Silicone 7207 and Silicone 7158 (manufactured by the Union Carbide Corporation); SF1202 (manufactured by General Electric).

Compositions of the present invention may also contain a powdered filler. Illustrative of this category are starches, talc, fumed silica (e.g. Cab-O-Sil from the Cabot Corporation), finely divided silica (e.g. sodium silicate), sodium bicarbonate, magnesium aluminum silicate, clays and mixtures thereof. Most preferred and effective are corn starch and modified starches, especially aluminum starch octenyl succinate, commercially available from the National Starch & Chemical Company under the trademark Dry Flo®.

Amounts of the powdered filler will range from 1 to 40%, preferably from 10 to 35%, optimally from 15 to 30% by weight.

Optionally included within the cosmetic creams of the present invention is that of a non-volatile $C_{12}$–$C_{40}$ hydrocarbon. Amounts of this material may range from 1 to 40%, preferably from 5 to 25%, optimally from 10 to 20% by weight.

The non-volatile hydrocarbon should have a viscosity of at least 10 cs at 25° C., preferably ranging from 10 to 100,000 cs at 25° C. The $C_{12}$–$C_{40}$, preferably $C_{20}$–$C_{40}$ hydrocarbon may either be saturated or unsaturated. Examples include dodecane, tridecane, tetradecane, pentadecane, hexadecane, heptadecane, octadecane, nonadecane, ecosane, heneicosane, docosane, tricosane, tetracosane, pentacosane, isomers of these compounds and mixtures thereof. Most preferred is polydecene available from the Ethyl Corporation under the Ethylflo trademark.

Inert particulates may also be included in cosmetic creams of the present invention. Illustrative of such materials are the polyolefins (such as polyethylene and polypropylene) and nylon. Most preferred are the spherical or non-spherical polyethylene powders. Amounts of these materials may range from 0.1 to 20%, preferably from 1 to 10% by weight.

Waxes may also be incorporated in compositions of the present invention. Animal origin waxes include beeswax, spermaceti, lanolin and shellac wax. Vegetable origin waxes include carnauba, candelilla, bayberry and sugarcane wax. Amounts of the wax may range from 0.5 to 30% by weight.

Most preferably compositions of the present invention will be creams and have a cone penetration value ranging from 2 to 36 mm, preferably from 10 to 25 mm, optimally from 12 to 20 mm as measured in the Standard Test Method for Cone Preparation of Petrolatum (ASTM D 937).

Advantageously, compositions of the present invention will be anhydrous. By the term "anhydrous" is meant an amount of free water ranging from 0 to 5%, preferably no higher than 3% by weight. Water complexed with aluminum salts may also be present but is not included within the term anhydrous.

The following examples will more fully illustrate embodiments of this invention, all percentages being by weight unless otherwise noted.

EXAMPLE 1

A variety of different silicone and non-silicone thickeners were evaluated as comparisons to the elastomers of the present invention. The tested formulations are set forth under Table I.

TABLE I

| | Formulation | | | | | | | |
|---|---|---|---|---|---|---|---|---|
| | WEIGHT % | | | | | | | |
| COMPONENT | A | B | C | D | E | F | G | H |
| DC 245 (cyclo-methicone) | 70.0 | 68.5 | 67.0 | 63.0 | 63.0 | 63.0 | 63.0 | 63.0 |
| AZAG | 26.0 | 26.0 | 26.0 | 26.0 | 26.0 | 26.0 | 26.0 | 26.0 |
| GE 1229 (25% elastomer in cyclo-methicone) | 4.0 | — | — | — | — | — | — | — |
| Silica | — | 5.5 | 7.0 | — | — | — | — | — |
| Stearyl Alcohol | — | — | — | 11.0 | — | — | — | — |
| Castor Wax | — | — | — | — | 11.0 | — | — | — |
| Silicone Wax SF1632 | — | — | — | — | — | 11.0 | — | — |
| Hydroxy-stearic acid | — | — | — | — | — | — | 11.0 | — |
| Silicone Wax SF1642* | — | — | — | — | — | — | — | 11.0 |

*SF1642 is 75% silicone/$C_{30}$ wax and 25% $C_{30}$ wax.

The formulations were prepared by first blending the GE 1229 with cyclomethicone, then passing the blend through a Sonolator to reduce particle size. Heat was applied as necessary to melt the waxes. Thereafter the AZAG was added into the mixture. Resultant formulations were poured or scooped into containers.

Formulation C was too thick to make an acceptable cream. Formulations E and G were non-homogeneous systems apparently because of insolubility between the wax and cyclomethicone. Formulation F was too soft for utilization as an underarm product.

Two test methods were utilized to evaluate leakage. The first is a modified paper chromatography method and the second is a finished product/package test.

In the paper chromatography test, a series of 10 cc beakers were filled with test product (Formulations A, B, D and H). These were then placed into a chromatography development chamber. Instead of standard chromatography paper, fragrance blotter paper 25×6 inches was employed because it is commercially available pre-cut with two measurement lines. The blotters were immersed in product up to the first line. They were allowed to stay in the development chamber for one hour. Leakage was then measured as the distance from the first line to the leading edge of the liquid front. Results of the chromatography test are reported in Table II.

TABLE II

Chromatography Test

| FORMULATION | DISTANCE OF SPREAD (mm) |
|---|---|
| A | 15 |
| B | 58 |
| D | 89 |
| H | 78 |

From Table II, it is seen that formulation A containing the elastomer exhibited the best results. Cyclomethicone is the component which moves furthest along the blotter. With the elastomer as a structurant, cyclomethicone was inhibited from breaking away to a more substantial extent than in formulations with other structurants (i.e. silica, stearyl alcohol or Silicone Wax SF 1642).

Leakage potential was also evaluated through a freeze/heat study. Each of the formulations was filled into a clicker stick dispenser of the type described in U.S. Pat. No. 5,573,341 (Iaia). The samples were then placed in a freezer for one hour. Thereafter they were moved to a 120° F. (49° C.) oven and left over night. Results are as reported in Table III. It is seen that only Formulation A appeared satisfactory.

TABLE III

Freeze/Heat Study

| FORMULATION | LEAKAGE |
|---|---|
| A | No signs of leakage |
| B | Leakage evident at bottom |
| D | Product separated |
| H | Product separated |

EXAMPLES 2–8

Illustrative of compositions falling within the present invention are the formulations recorded in Table IV.

TABLE IV

| | EXAMPLE (WEIGHT %) | | | | | | |
|---|---|---|---|---|---|---|---|
| COMPONENT | 2 | 3 | 4 | 5 | 6 | 7 | 8 |
| Cyclomethicone | 29.7 | 29.7 | 29.7 | 29.7 | 68.0 | 50.0 | 50.0 |
| GE 1229 | 13.5 | 13.5 | 13.5 | 13.5 | 6.0 | 2.0 | 1.0 |
| Polydecene 364 | 10.8 | 10.8 | 10.8 | 10.8 | — | 10.8 | 10.8 |
| AZAG | 26.0 | 26.0 | 26.0 | — | 26.0 | 26.0 | 26.0 |
| Triclosan | — | — | — | 2.0 | — | — | — |
| Corn Starch | 20.0 | — | 18.5 | 20.0 | — | 11.2 | — |
| Talc | — | 20.0 | — | 20.0 | — | — | 10.2 |
| Fumed Silica | — | — | 1.5 | 4.0 | — | — | 1.0 |

EXAMPLES 9–10

Other compositions within the present invention are the formulations recorded in Table V.

TABLE V

| | EXAMPLE (WEIGHT %) | |
|---|---|---|
| COMPONENT | 9 | 10 |
| GE 1229 | 15.6 | 9.1 |
| DC 245 | 44.7 | 33.8 |

TABLE V-continued

| COMPONENT | EXAMPLE (WEIGHT %) | |
|---|---|---|
| | 9 | 10 |
| DC 246 | 10.7 | 7.6 |
| AZAG | 26.0 | 26.0 |
| Silicone Wax SF 1632 | 3.5 | 3.0 |
| Fragrance | 0.5 | 0.5 |
| Corn Starch | — | 20.0 |

The foregoing description and examples illustrate selected embodiments of the present invention. In light thereof, various modifications would be suggested to one skilled in the art, all of which are within the spirit and purview of this invention.

What is claimed is:

1. A underarm treatment composition comprising:
   (i) an underarm active present in an effective amount to inhibit odor or to reduce perspiration;
   (ii) from 0.1 to 5.5% by weight of a crosslinked non-emulsifying siloxane elastomer;
   (iii) from 10 to 80% by weight of a volatile siloxane.

2. A composition according to claim 1 wherein the crosslinked non-emulsifying siloxane elastomer is formed from a divinyl monomer reacting with Si—H linkages of a siloxcine backbone.

3. The composition according to claim 1 which is a cream having a cone penetration value ranging from 2 to 36 mm.

4. The composition according to claim 1 further comprising from 1 to 40% by weight of a non-volatile $C_{12}$–$C_4O$ hydrocarbon.

5. The composition according to claim 4 wherein the hydrocarbon is polydecene.

6. The composition according to claim 1 wherein the underarm active is present from 0.1 to 70% by weight.

7. The composition according to claim 1 wherein the underarm active is an astringent salt of a metal selected from the group consisting of aluminum, zirconium, zinc and mixtures thereof.

8. The composition according to claim 1 further comprising from 0.5 to 30% by weight of a wax.

9. The composition according to claim 1 wherein the elastomer is present from 1 to 5% by weight.

10. The composition according to claim 1 wherein the elastomer is present from 1 to 3% by weight.

11. The composition according to claim 1 wherein the elastomer has an average particle size ranging from 0.2 to 10 micron.

12. The composition according to claim 1 wherein the elastomer is vinyl dimethicone/methicone cross polymer.

13. The composition according to claim 1 wherein the elastomer is crosslinked stearyl methyl dimethyl siloxane copolymer.

14. The composition according to claim 1 wherein the elastomer has a viscosity ranging from 300 to 20,000 cps at 25° C. as measured by a Brookfield LV Viscometer on a size base 4 bar at 60 rpm for 15 seconds.

* * * * *

UNITED STATES PATENT AND TRADEMARK OFFICE
CERTIFICATE OF CORRECTION

PATENT NO. : 5,922,308
DATED : July 13, 1999
INVENTOR(S) : Brewster et al.

It is certified that error appears in the above-indentified patent and that said Letters Patent is hereby corrected as shown below:

Title page, item [73],
    Assignee: change "Chesebrough-Pond's USA Co.,."

to read -- Chesebrough-Pond's USA Co., Division of Conopco, Inc. --

Signed and Sealed this

Twenty-sixth Day of December, 2000

*Attest:*

Q. TODD DICKINSON

*Attesting Officer*          *Director of Patents and Trademarks*